United States Patent [19]

Potter et al.

[11] Patent Number: 4,484,949

[45] Date of Patent: Nov. 27, 1984

[54] CEMENT COMPOSITIONS

[75] Inventors: William D. Potter, Bishops Stortford; Andrew C. Barclay, Harlow; Reginald Dunning, Parbold, near Wigan; Richard J. Parry, Southport, all of England

[73] Assignee: Smith & Nephew Research Limited, England

[21] Appl. No.: 392,667

[22] Filed: Jun. 28, 1982

[30] Foreign Application Priority Data

Jul. 3, 1981 [GB] United Kingdom ................. 8120581

[51] Int. Cl.$^3$ .............................................. C04B 25/00
[52] U.S. Cl. .................... 106/85; 128/87 R; 128/90 R; 501/73
[58] Field of Search ...................... 106/35, 85; 501/73; 128/87 R, 90 R

[56] References Cited

U.S. PATENT DOCUMENTS 4,108,169   8/1978   Parker ................................ 128/90

*Primary Examiner*—James Poer
*Attorney, Agent, or Firm*—Jacobs & Jacobs

[57] ABSTRACT

A water hardenable cement composition comprising a fluorine-free calcium alumino silicate glass in particulate form in which the individual particulates have a particle size of less than 100 microns consisting essentially of 25–35% silica, 27–35% calcium oxide, 25–40% alumina, up to 4% of an alkali metal oxide, up to 5% of titania, the total amount of alkali metal oxide and titania being 0.5–9%, wherein the ratio of calcium oxide to silica is 0.7:1 to 1:0-7, together with a polycarboxylic acid.

20 Claims, No Drawings

CEMENT COMPOSITIONS

The invention relates to water-hardenable compositions comprising a calcium aluminosilicate glass in a finely divided form together with a polycarboxylic acid, which when mixed with water set to form a solid mass. Cement compositions of the invention are particularly suitable for use in splinting agents. The invention also relates to the manufacture and use of such cement compositions.

It is now well established that splinting bandages can be prepared from water hardenable cement compositions in which the reactive components are a glass and a polycarboxylic acid. The most successful version of this form of bandage is described in British Pat. No. 1,554,554 and the glasses used in the cements are described in British Pat. No. 1,554,555. One example of such a bandage using such a glass is available as "CRYSTONA" from T. J. Smith and Nephew of Welwyn Garden City and Hull, U.K. This existing product has many excellent properties resulting from the use of a calcium fluoroaluminosilicate glass as described in British Pat. Nos. 1554554/5, to provide a composition which remains workable for a period (the gel time) sufficient to enable the bandage to be placed in position, but then sets quite rapidly. Unfortunately the need to incorporate quantities of fluorine in the glass to achieve an acceptable gel time and set time adds substantially to the cost of the production process. This is because fluorine is regarded as an atmospheric pollutant and glasses containing significant quantities of fluorine need to be made under strictly controlled and hence expensive operating conditions in order to protect the environment.

Cement compositions have now been discovered which do not require the presence of a glass which contains fluorine in order to achieve acceptable gel and set times when used in such a cement composition.

Accordingly the present invention provides a water-hardenable cement composition comprising a calcium aluminosilicate glass in finely divided form containing 25 to 35% silica, 27 to 35% calcium oxide, 25 to 40% alumina, 0 to 4% of alkali metal oxide selected from lithium oxide, sodium oxide and potassium oxide and 0 to 5% titanium oxide wherein the total amount of lithium, sodium, potassium and titanium oxides is 0.5 to 9%; together with a polycarboxylic acid.

All percentages herein are on a weight/weight basis unless otherwise stated.

As is conventional in the glass making art the glass for use in the cement compositions of this invention may also contain small quantities of compatible materials which do not affect the melting or performance of the glass to an unacceptable extent. Generally the presence of such other agents is not envisaged as desirable and preferably the glass is free of fluorine containing materials.

Favoured glasses for use in the cement compositions of this invention include those which contain in total 1.5 to 5% of alkali metal and titanium oxides. Moreover, sodium oxide is generally the preferred alkali metal oxide.

Certain especially favoured glasses for use in the cement compositions of this invention are those containing 28 to 34% silica, 28 to 34% calcium oxide, 30 to 40% alumina and 0 to 4% of sodium oxide and 0 to 5% of titanium oxide with the proviso that the total amount of sodium and titanium oxides is 1.5 to 5%.

Preferably if the glass for use with the cement compositions of this invention is free of sodium, potassium and lithium oxide then it will contain 1 to 4% of titanium oxide. Preferably, if the glass for use in cement compositions of this invention is free of titanium oxide it will not contain more than 3% in total of sodium, potassium and lithium oxides, that is contains from 1.5 to 3% in total of sodium, potassium and lithium oxides.

Aptly the glasses for use in the cement compositions of this invention will contain calcium oxide and silica in a ratio 0.7:1 to 1:0.7, more suitably 0.8:1 to 1:1.1 and preferably about 0.9:1 to 1:1.

A favoured glass for use in the cement compositions of the present invention consists essentially of 30 to 34% of silica, 28 to 33% of calcium oxide, 32 to 40% of alumina and 1 to 3% of sodium oxide. A preferred glass consists essentially of 31.4% silica, 28.7% calcium oxide, 38.1% alumina and 1.8% sodium oxide.

For use in the cement compositions of this invention the glasses will be in finely divided form. Aptly the glasses will have a surface area of 1250 to 2000 $cm^2/g$ and more aptly 1500 to 1850 $cm^2/g$. Normally the finely divided glass will be in the form of a finely divided powder. Generally the individual particles will be less than 100 microns and preferably less than 50 microns.

The glasses may be prepared by melting together silica, alumina, calcium oxide and the required alkali metal and/or titanium oxide in the previously described amounts. If desired precursors of such oxides may be employed. Generally melting of the mixtures occurs within the range 1350° C. to 1600° C., with the especially favoured glasses referred to above melting generally towards the lower end of this temperature range.

After solidification on cooling the glass can be converted to the desired finely divided form in conventional manner such as ball milling, pestle-and-mortar grinding or the like with sieving if desired.

The glass in its finely divided form may be mixed with polycarboxylic acid or a polymeric precursor thereof for example a polycarboxylic acid anhydride for use in a water-hardenable cement composition of the present invention.

Favourably the calcium aluminosilicate glass forms 30 to 45% of the composition. More favourably the calcium aluminosilicate glass forms 33 to 38% of the of the composition. Preferably the calcium aluminosilicate glass forms 35 to 37% of the composition.

The polycarboxylic acids used in the cement compositions may be homopolymers of unsaturated monocarboxylic acids or unsaturated dicarboxylic acids or copolymers between any two or more of these acids or copolymers of one or more of these acids with one or more other ethylenically unsaturated monomers. Suitable unsaturated carboxylic acids for the present invention include acrylic, itaconic, mesaconic, citraconic or maleic acids. The preferred polycarboxylic acid is the homopolymer of acrylic acid which will be referred to hereinafter as polyacrylic acid.

The polyacrylic acid for use in this invention will normally have a molecular weight of from 1000 to 1,000,000. Polyacrylic acids having a molecular weight of 50,000 to 500,000 are preferred.

Suitably the polycarboxylic acid forms 20 to 30% of the dry composition. More suitably the polycarboxylic acid forms 22 to 28% of the composition. Preferably the polycarboxylic acid forms 23 to 25% of the composition.

Usually the cement compositions of this invention will include a monomeric acid containing at least two carboxyl groups or a hydroxy carboxylic acid. The presence of an acid of this type serves to maximise the desirable properties of the composition of this invention with regard to gel time and set time. Suitable organic acids include tartaric, succinic, oxalic, citric and ascorbic acids. The preferred acid is tartaric acid.

A particularly suitable amount of this acid to be present in the cement compositions of the invention is 1 to 4% and is preferably 2%.

Usually the dry cement compositions of the present invention will include 5 to 10% of sodium chloride to improve the shrinkage characteristics of the composition while setting. More suitably the composition will contain 6 to 8% of sodium chloride. Preferably about 7% of sodium chloride is employed.

Usually a thickening agent will be employed in cement compositions of the present invention. Suitable thickening agents include cellulose derivatives or a modified bentonite clay. Preferred thickening agents are hydroxypropylcellulose or a modified bentonite clay or a mixture thereof.

Thickening agents will suitably comprise up to 4% of the cement compositions of the invention and preferably will comprise 1 to 3% of the compositions.

Generally the cement compositions of the present invention will include a particulate material as a filler. Suitably alumina may be used as a filler without causing undue weakening of the final set cements which are formed from the composition. Most suitably 25 to 35% of alumina may be used in the composition. More favourably 27 to 32% and preferably 28.4% of alumina is used in the composition.

The various components of the water-hardenable cement composition are generally provided in the form of fine particles. The particle size of the finely divided glass has been described above. The polyacrylic acid particle size will generally be in the range 5 to 150 microns and more suitably in the range 10 to 100 microns. The organic acid and sodium chloride particles will generally be in the size range 2 to 70 microns. The alumina particles will have a mean specific surface area of powder greater than 15,000 cm$^2$/g and preferably greater than 20,000 cm$^2$/g with at least 80% of the particles less than 10 microns and preferably 90% of the particles are less than 10 microns in size.

The various components of the cement compositions of this invention may be blended together in a conventional manner, for example by dry powder blending.

When water is added to a cement composition of the present invention as described above it will first gel and then set. It has been found that to give desirable properties for use on a carrier as a splinting bandage the gel time is suitably in the range 65 to 130 seconds and is preferably in the range 80 to 120 seconds. The corresponding set time is suitably in the range from 5 to 18 minutes and preferably is from 10 to 15 minutes. As the gel time and set time may vary independently of each other as the components of the composition may vary it is convenient to consider the set time to gel time ratio as a criterion of acceptability for use in a splinting bandage. It is preferred that this ratio lies in the range of 6:1 to 14:1 and preferably is in the range 7:1 to 10:1.

From the foregoing it will be appreciated that favoured water-hardenable cement compositions of this invention consist essentially of 30 to 45% of a calcium aluminosilicate glass, 23 to 25% of a polycarboxylic acid, 27 to 32% of alumina, 6 to 8% sodium chloride, 1 to 4% organic acid, 1 to 3%, as a thickener, of a mixture of hydroxypropylcellulose and modified bentonite clay.

A preferred water-hardenable cement composition comprises 36.3% of a calcium aluminosilicate glass, 24.3% polyacrylic acid, 28.4% alumina, 7% sodium chloride, 2.0% tartaric acid, 1.65% hydroxypropyl cellulose and 0.35% of a modified bentonite clay.

Although the water-hardenable cement compositions of this invention may be used for a wide range of cement purposes, they are of particular use in the preparation of splinting materials.

Accordingly the present invention also provides a water-hardenable splinting material comprising a carrier loaded with a water-hardenable cement composition containing a calcium aluminosilicate glass in finely divided form and consisting of 25 to 35% silica, 27 to 35% calcium oxide, 25 to 40% alumina, 0 to 4% lithium, potassium, sodium and titanium oxides wherein the total amount of lithium, potassium, sodium and titanium oxides is 1 to 9% together with a solid particulate polymer chosen from the group consisting of polycarboxylic acids.

For use in splinting, the cement composition is loaded on a carrier, normally an openwork substrate (woven or non-woven) of which a Leno gauze of polyester and cotton is preferred. Loading may be by way of coating or impregnation.

Normally the carrier is loaded at a weight of from 200 to 500 g/m$^2$ of the cement composition.

The splinting material of this invention is generally in the form of a bandage provided rolled on a support core, for example a cruciform core, so that in use it is dipped into water for a few seconds, squeezed and wrapped around the affected limb or the like and allowed to gel and set to a hard material.

This invention also provides a process for the preparation of the water-hardenable splinting material which process comprises loading an openwork fabric with a slurry of the water-hardenable cement compositions of this invention in a volatile organic liquid and thereafter removing the volatile organic liquid.

The organic liquid can be any unreactive liquid which does not cause gellation and which may be removed by evaporation. A preferred liquid is methylene chloride. Normally the weight of methylene chloride used is about half the weight of water-hardenable cement composition.

It will be appreciated that, when the cement compositions of glass and polyacrylic acids in accordance with the invention are used in products other than splinting materials, it may be desirable to vary the nature and amounts of any additional components used.

EXAMPLE 1

Calcium Aluminosilicate Glass

A calcium aluminosilicate glass was prepared from the following ingredients:

| | |
|---|---|
| Silica | 250.8 g |
| Calcium carbonate | 410.3 g |
| Aluminium hydroxide | 466.8 g |
| Sodium carbonate | 24.35 g | to give a glass of the following composition expressed as % w/w

| Silica | 31.4% |
|---|---|
| Calcium oxide | 28.7% |
| Alumina | 38.1% |
| Sodium oxide | 1.8% |

The ingredients were melted in a crucible at 1500° C. and when molten stirred. The molten glass was then poured into water.

EXAMPLE 2

Grinding of Calcium Aluminosilicate Glass

A portion of calcium aluminosilicate glass prepared in Example 1 was taken and ground in a mechanical pestle and mortar for one hour. Suitable mechanical pestle and mortars are available from the Pascall Engineering Co. Ltd. The powder obtained was sieved through a coarse sieve to remove the largest particles of glass and the remaining powder was re-sieved and the fraction having a particle size less than 45 microns was isolated for use in a water-hardenable cement composition.

EXAMPLE 3

Water-hardenable Cement Composition

A water hardenable cement composition was formulated as follows:

| Calcium aluminosilicate glass of Example 2 | 36.3% |
|---|---|
| Polyacrylic acid | 24.3% |
| Alumina | 28.4% |
| Sodium chloride | 7.0% |
| Tartaric acid | 2.0% |
| Hydroxypropyl cellulose | 1.65% |
| Modified bentonite clay | 0.35% |

The dry particulate materials were mixed and a portion taken to be assessed for gel and set time. To determine gel time and set time, water at 20° C. was added to a container such that the ratio of water to powder was 1:2 by weight. A portion of the homogeneous wet mix was poured into a cylindrical mould of 25.4 mm internal diameter, 2 mm deep, resting on a glass plate, all the apparatus being kept at 20° C. and in an atmosphere having a relative humidity of 65%. The portion of the mix in the container was used to determine the gel time. The composition was deemed to have gelled when on gentle manipulation with a spatula the composition failed to flow from the end of the spatula. The gel time extended from the time of mixing until gelling. The composition was deemed to have set when a Gilmore 'final' needle (of weight 454 g, diameter 1.06±0.05 mm, cylindrical for 4.8 mm from its plane end at right angles to the rod) lowered vertically onto the horizontal surface in the mould and allowed to rest thereon for approximately five seconds left no perceptible indentation. The set time extended from mixing to setting. Each timing was repeated three times and an average value taken.

The gel time of this composition was 94 seconds and the set time 12.1 minutes to give a set to gel time ratio of 7.7.

EXAMPLE 4

Water Hardenable Cement Bandage

A bandage useful for a splinting application was prepared using a portion of the water-hardenable cement composition described in Example 3.

Hydroxypropyl cellulose (2%) was dissolved in methylene chloride. The dry particulate water-hardenable cement composition was added to this solution until on mixing a slurry was formed which had a solids content of 50%.

The slurry was placed in an application box with a flexible doctor blade and ridging bar and spread at a loading of 300 g/m$^2$ on a Leno gauze bandage of cotton polyester weave about 9 meters long and 8 cm wide. The bandage was air dried and wrapped around a conventional cruciform core.

EXAMPLES 5 to 24

Calcium aluminosilicate glasses were prepared as in Example 1 and water-hardenable cement compositions prepared and tested as described in Examples 2 and 3. The following Table describes the composition and properties of these glasses.

TABLE

| Example | Silica | Calcium oxide | Alumina | Sodium oxide | Titanium oxide | Gel (Secs) | Set (Mins) | Set time Gel time |
|---|---|---|---|---|---|---|---|---|
| 5 | 33.2 | 29.9 | 35.0 | 1.8 | 0 | 70 | 10.4 | 8.9 |
| 6 | 31.3 | 29.3 | 37.5 | 1.8 | 0 | 107 | 14.7 | 8.2 |
| 7 | 31.0 | 29.8 | 36.2 | 1.8 | 1.2 | 132 | 18 | 8.2 |
| 8 | 33.1 | 29.8 | 34.8 | 0 | 2.3 | 142 | 20 | 8.5 |
| 9 | 32.0 | 31.8 | 33.9 | 0 | 2.3 | 116 | 16.2 | 8.4 |
| 10 | 31.1 | 29.0 | 37.2 | 2.7 | 0 | 81 | 11.2 | 8.3 |
| 11 | 30.5 | 29.3 | 35.5 | 3.6 | 1.1 | 70 | 11.2 | 9.6 |
| 12 | 32.5 | 29.2 | 34.2 | 1.8 | 2.3 | 94 | 13.6 | 8.7 |
| 13 | 31.3 | 32.0 | 32.5 | 1.8 | 2.4 | 84 | 10.1 | 7.2 |
| 14 | 30.4 | 31.9 | 32.4 | 1.8 | 3.4 | 118 | 15.3 | 7.8 |
| 15 | 29.4 | 31.8 | 32.4 | 1.8 | 4.7 | 157 | 22 | 8.5 |
| 16 | 33.9 | 33.3 | 30.4 | 0 | 2.4 | 92 | 12.1 | 7.9 |

| Example | Silica | Calcium oxide | Alumina | Sodium oxide | Titanium oxide | additional constituents | Gel (secs) | Set (mins) | Set time Gel time |
|---|---|---|---|---|---|---|---|---|---|
| 17 | 28.8 | 33.0 | 30.1 | 0 | 3.0 | 5.1 B$_2$O$_3$ | 98 | 17.5 | 10.7 |
| 18 | 33.2 | 29.9 | 35.0 | 0 | 1.8 | 0 | 70 | 10.4 | 8.9 |
| 19 | 31.7 | 29.6 | 37.9 | 0.9 | 0 | 0 | 89 | 17.0 | 11.5 |
| 20 | 30.8 | 28.8 | 36.8 | 3.6 | 0 | 0 | 65 | 8.1 | 7.5 |
| 21 | 31.2 | 28.6 | 38.0 | 0.9 | 0 | 1.4 K$_2$O | 47 | 11.0 | 14.0 |
| 22 | 31.6 | 29.0 | 38.5 | 0 | 0 | 0.9 Li$_2$O | 85 | 12.3 | 8.7 |

TABLE-continued

| 23 | 31.1 | 28.5 | 37.8 | 0   | 0 | 2.7 K$_2$O | 61 | 9.0 | 8.9 |
|----|------|------|------|-----|---|------------|----|-----|-----|
| 24 | 31.4 | 28.1 | 40.0 | 0.5 | 0 | 0          | 80 | 9.6 | 7.2 |

What is claimed is:

1. A water-hardenable cement composition comprising a fluorine-free calcium alumino silicate glass in particulate form in which the individual particles have a particle size of less than 100 microns, which consists essentially of 25 to 35% silica, 27 to 35% calcium oxide, 25 to 40% alumina, an alkali metal oxide in an amount not more than 4% selected from lithium, oxide, sodium oxide and potassium oxide and titanium oxide in an amount not more than 5%, wherein the total amount of lithium, sodium, potassium and titanium oxides is 0.5 to 9% and wherein the ratio of calcium oxide to silica is 0.7:1 to 1:0.7; together with a polycarboxylic acid.

2. A water-hardenable cement composition as claimed in claim 1 in which the glass comprises from 30 to 45% of the composition.

3. A water-hardenable cement composition as claimed in claim 1 in which the polycarboxylic acid is a homopolymer of an unsaturated monocarboxylic or unsaturated dicarboxylic acid or a copolymer between any two or more of these acids or copolymers of one or more of these acids with one or more ethylenically unsaturated monomers.

4. A water-hardenable cement composition as claimed in claim 1 in which the polycarboxylic acid comprises from 20 to 30% of the composition.

5. A water-hardenable cement composition as claimed in claim 1 which additionally contains from 25 to 35% of a filler.

6. A water-hardenable cement composition comprising a fluorine-free calcium aluminosilicate glass in particulate form in which the individual particles have a particle size of less than 100 microns, which consists essentially of 30 to 34% of silica, 28 to 33% of calcium oxide, 32 to 40% of alumina and 1 to 3% of sodium oxide together with a polycarboxylic acid.

7. A water-hardenable cement composition which consists essentially of 30 to 45% of the calcium aluminosilicate glass according to claim 6, 23 to 25% of a polycarboxylic acid, 27 to 32% of alumina, 6 to 8% sodium chloride, 1 to 4% of an organic acid selected from the group consisting of a monomeric acid containing at least two carboxyl groups or a hydroxycarboxylic acid and 1 to 3% of a mixture of hydroxypropylcellulose and modified bentonite clay.

8. A water-hardenable cement according to claim 7, wherein the amount of the calcium aluminosilicate glass is 33 to 38% of the composition.

9. A water-hardenable cement according to claim 8, wherein the amount of the calcium aluminosilicate glass is 35 to 37% of the composition.

10. A water-hardenable cement composition comprising a fluorine-free calcium alumino silicate glass in particulate form in which the individual particles have a particle size of less than 100 microns, which consists essentially of 25 to 35% silica, 27 to 35% calcium oxide, 25 to 40% alumina and 1 to 4% titanium oxide and wherein the ratio of calcium oxide to silica is 0.7:1 to 1:0.7; together with a polycarboxylic acid.

11. A water-hardenable cement composition as claimed in claim 10, in which the glass comprises from 30 to 45% of the composition.

12. A water-hardenable cement composition as claimed in claim 10, in which the polycarboxylic acid is a homopolymer of an unsaturated monocarboxylic or unsaturated dicarboxylic acid or a copolymer between any two or more of these acids or copolymers of one or more of these acids which one or more ethylenically unsaturated monomers.

13. A water-hardenable cement composition as claimed in claim 10, in which the polycarboxylic acid comprises from 20 to 30% of the composition.

14. A water-hardenable cement composition as claimed in claim 10 which additionally contains from 25 to 35% of a filler.

15. A water-hardenable cement composition comprising a fluorine-free calcium alumino silicate glass in particulate form in which the individual particles have a particle size of less than 100 microns, which consists essentially of 25 to 35% silica, 27 to 35% calcium oxide, 25 to 40% alumina and 1.5 to 3.0% in total of sodium, potassium and lithium oxides and wherein the ratio of calcium oxide to silica is 0.7:1 to 1:0.7; together with a polycarboxylic acid.

16. A water-hardenable cement composition is claimed in claim 15, in which the glass comprises from 30 to 45% of the composition.

17. A water-hardenable cement composition as claimed in claim 15, in which the polycarboxylic acid is a homopolymer of an unsaturated monocarboxylic or unsaturated dicarboxylic acid or a copolymer between any two or more of these acids or copolymer of one or more of these acids with one or more ethylenically unsaturated monomers.

18. A water-hardenable cement composition as claimed in claim 15, in which the polycarboxylic acid comprises from 20 to 30% of the composition.

19. A water-hardenable cement composition as claimed in claim 15, which additionally contains from 25 to 35% of a filler.

20. A method of manufacturing a water-hardenable splinting material wherein a carrier of a woven or nonwoven substrate is contacted in order to load the carrier, with a slurry in a volatile organic liquid of a water hardenable cement composition which consists essentially of 30 to 45% of the fluorine-free calcium aluminosilicate glass according to claim 15, 23 to 25% of polycarboxylic acid, 27 to 32% of alumina, 6 to 8% sodium chloride, 1 to 4% of an organic liquid selected from the group consisting of a monomeric acid containing at least two carboxyl groups or a hydroxycarboxylic acid and 1 to 3% of a mixture of hydroxypropyl cellulose and modified bentonite clay; and thereafter removing the volatile organic liquid.

* * * * *